US009572605B2

(12) United States Patent
Shipp

(10) Patent No.: US 9,572,605 B2
(45) Date of Patent: Feb. 21, 2017

(54) SURGICAL INSTRUMENT AND METHOD

(71) Applicant: Warsaw Orthopedic, Inc., Warsaw, IN (US)

(72) Inventor: Kenneth Shipp, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 836 days.

(21) Appl. No.: 13/647,798

(22) Filed: Oct. 9, 2012

(65) Prior Publication Data
US 2014/0100616 A1 Apr. 10, 2014

(51) Int. Cl.
*A61B 17/70* (2006.01)
*A61B 17/88* (2006.01)

(52) U.S. Cl.
CPC ........ *A61B 17/7082* (2013.01); *A61B 17/7076* (2013.01); *A61B 17/888* (2013.01); *A61B 17/8875* (2013.01); *A61B 17/8877* (2013.01); *A61B 17/8883* (2013.01); *A61B 17/8886* (2013.01); *A61B 17/8888* (2013.01); *A61B 17/8891* (2013.01); *A61B 17/8894* (2013.01)

(58) Field of Classification Search
CPC ............ A61B 17/7076; A61B 17/7082; A61B 17/8875; A61B 17/8877; A61B 17/888; A61B 17/8883; A61B 17/8886; A61B 17/8888; A61B 17/8891; A61B 17/8894
USPC ........................................................ 606/916
See application file for complete search history.

(56) References Cited

U.S. PATENT DOCUMENTS

| 3,351,054 | A | 11/1967 | Florek |
| 3,835,858 | A * | 9/1974 | Hagen ........................... 606/180 |
| 5,096,213 | A | 3/1992 | Terwilliger et al. |
| 5,439,005 | A | 8/1995 | Vaughn |
| 5,476,467 | A | 12/1995 | Benoist |
| 5,888,200 | A * | 3/1999 | Walen ........................... 606/167 |
| 5,941,891 | A * | 8/1999 | Walen ........................... 606/167 |
| 7,559,927 | B2 * | 7/2009 | Shores et al. ................... 606/79 |
| D625,803 | S | 10/2010 | Studenec |
| 8,398,639 | B2 * | 3/2013 | Myers et al. ................... 606/79 |
| 8,439,922 | B1 * | 5/2013 | Arnold ............... A61B 17/7082 606/104 |
| 2003/0229351 | A1 | 12/2003 | Tidwell et al. |
| 2007/0005077 | A1 * | 1/2007 | Null ..................... A61B 17/862 606/104 |
| 2008/0243133 | A1 * | 10/2008 | Heinz ................... B25B 23/101 606/104 |
| 2009/0234395 | A1 * | 9/2009 | Hoffman ............ A61B 17/8875 606/86 A |
| 2009/0318972 | A1 * | 12/2009 | Jackson ........................ 606/264 |
| 2011/0245881 | A1 | 10/2011 | Mitchell |

(Continued)

*Primary Examiner* — Ellen C Hammond

(57) ABSTRACT

A surgical instrument includes a first member including an inner surface defining a passageway. The first member extends between a first end that defines a first opening and a second end that defines a second opening. A second member extends between a first end and a second end. A third member extends between a first end and a second end. The second end of the third member is releasably engageable with the first end of the second member within the passageway such that the first end of the first member prevents passage of the first end of the third member through the first opening and the second end of the first member prevents passage of the second end of the second member through the second opening. Systems and methods of use are disclosed.

20 Claims, 3 Drawing Sheets

(56) References Cited

U.S. PATENT DOCUMENTS

| | | | |
|---|---|---|---|
| 2012/0265259 A1* | 10/2012 | Laposta | A61B 17/8894 606/86 A |
| 2013/0150864 A1* | 6/2013 | Marik | A61B 17/8888 606/104 |
| 2013/0282019 A1* | 10/2013 | Bouliane | 606/104 |
| 2014/0100583 A1* | 4/2014 | Butler | A61B 17/7082 606/104 |

* cited by examiner

SURGICAL INSTRUMENT AND METHOD

TECHNICAL FIELD

The present disclosure generally relates to medical devices for the treatment of musculoskeletal disorders, and more particularly to a surgical system for delivering and/or fastening implants with a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attaching rods and plates to the exterior of two or more vertebral members. This disclosure describes an improvement over these prior art technologies.

SUMMARY

In one embodiment, in accordance with the principles of the present disclosure, a surgical instrument is provided. The surgical instrument includes a first member having an inner surface defining a passageway. The first member extends between a first end that defines a first opening and a second end that defines a second opening. A second member extends between a first end and a second end. A third member extends between a first end and a second end. The second end of the third member is releasably engageable with the first end of the second member within the passageway such that the first end of the first member prevents passage of the first end of the third member through the first opening and the second end of the first member prevents passage of the second end of the second member through the second opening.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
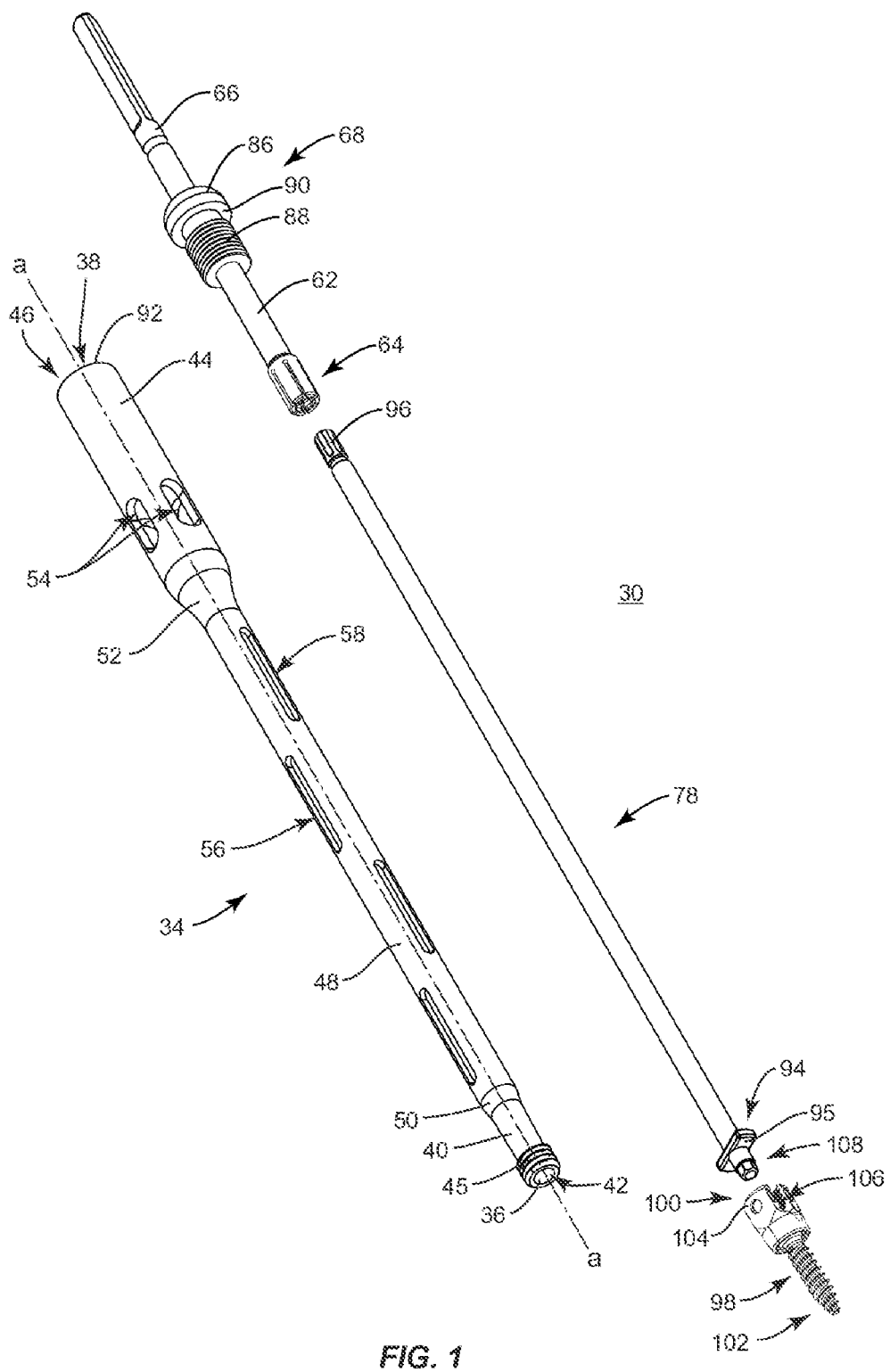
FIG. 1 is a perspective view of components of one particular embodiment of a surgical system in accordance with the principles of the present disclosure with parts separated.

The exemplary embodiments of a surgical system are discussed in terms of medical devices for the treatment of musculoskeletal disorders and more particularly, in terms of a surgical implant system for delivering and/or fastening implants with a surgical site and a method for treating a spine. In one embodiment, the system includes a surgical instrument having a T-bar element configured to engage an implant, such as, for example, a bone anchor or bone fastener. In one embodiment, the surgical instrument includes a housing and a drive shaft that includes a bottom drive shaft and a top drive shaft. In one embodiment, an end of the bottom drive shaft and an end of the top drive shaft each define a hexalobular driver for coupling components of the system. This configuration facilitates attachment of the drive shafts with the housing and/or removal of the drive shafts from the housing independently of one another for disassembly.

In one embodiment, the system includes a surgical instrument having a hexalobular driver assembly, which allows a shaft of the assembly to include two components. The driver assembly includes a T-bar portion that can be removed from a bottom of the shaft and a tri-flat portion that can be removed from a top of the shaft.

In one embodiment, the system includes a surgical instrument capable of disassembly to facilitate cleaning of each of the components of the surgical instrument. This configuration provides access to areas of the surgical instrument, including difficult to reach areas and/or inaccessible areas due to a surgical instrument's assembled configuration. It is envisioned that the surgical instrument is capable of disassembly and assembly. In one embodiment, the surgical instrument includes a collet style connection mechanism to facilitate disassembly and assembly. It is contemplated that the surgical instrument may be disassembled and assembled without additional tools or other instruments.

It is envisioned that the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
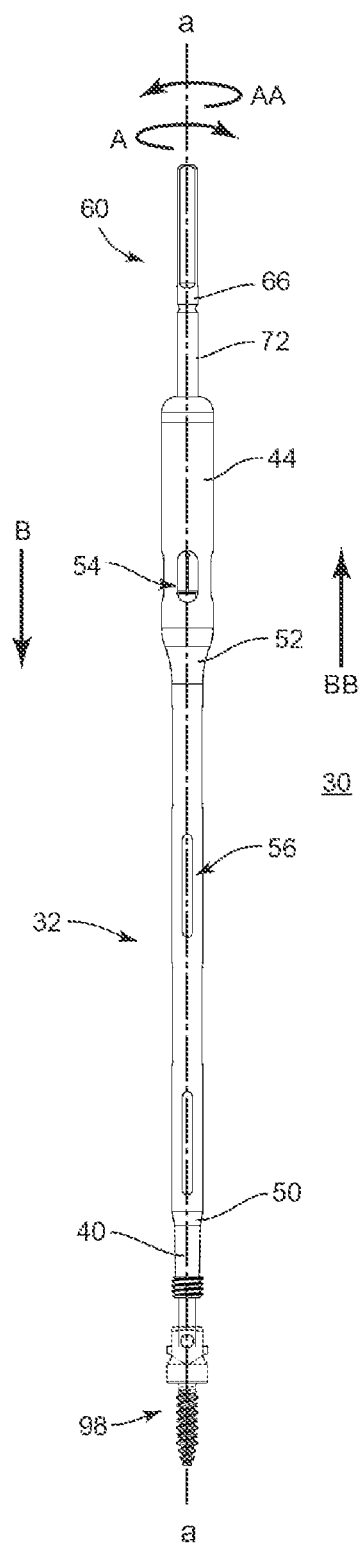
FIG. 2 is a side view of the components of the system shown in FIG. 1.
Figure 3:
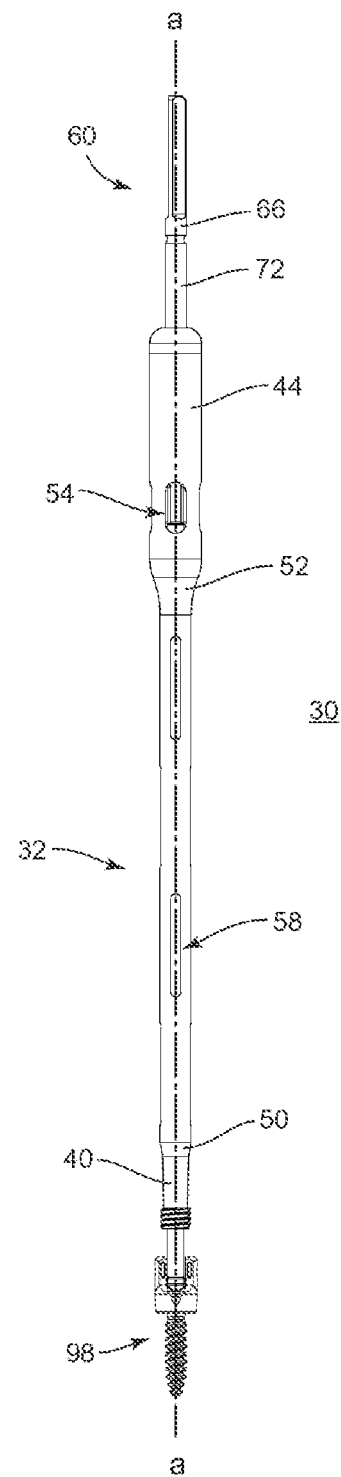
FIG. 3 is a side view of the components of the system shown in FIG. 1.
Figure 4:
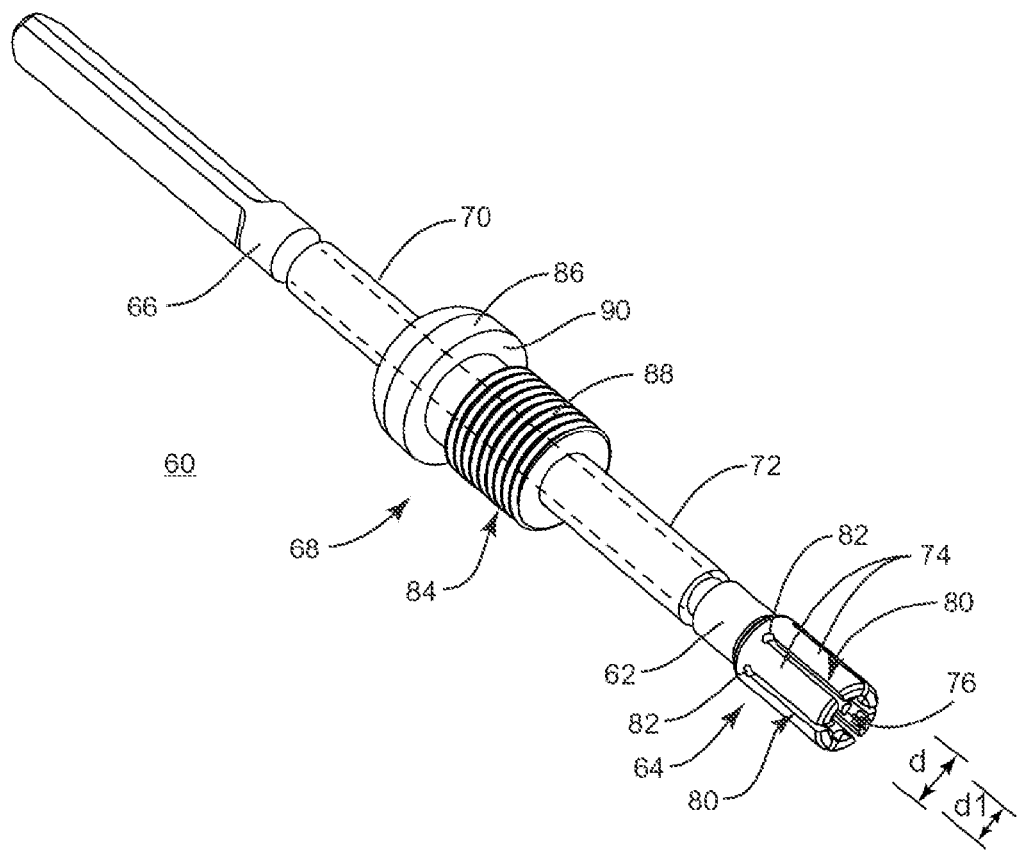
FIG. 4 is a perspective view, in part phantom, of components of the system shown in FIG. 1.
Figure 5:
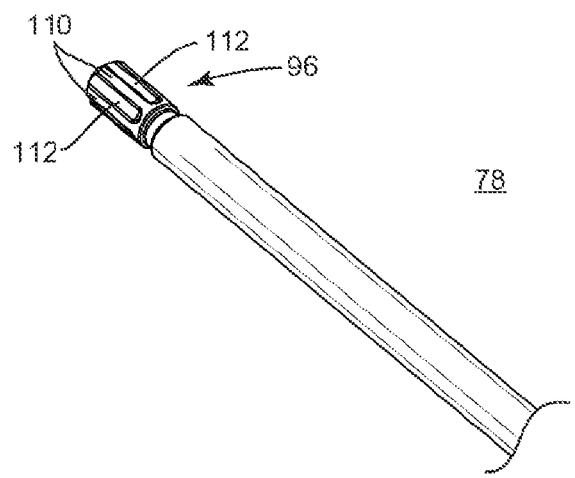
FIG. 5 is a break away perspective view of a component of the system shown in FIG. 1.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of a surgical implant system 30 including a surgical instrument 32, in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, aluminum, commercially pure titanium, titanium alloys, Grade 5 titanium, super-elastic titanium alloys, cobalt—chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open or mini-open, minimal access and/or minimally invasive including percutaneous surgical technique to deliver and fasten an implant, such as, for example, a bone fastener at a surgical site within a body of a patient, for example, a section of a spine. In one embodiment, the components of system 30 are configured to fix a spinal rod, connector and/or plate to a spine via a bone fastener for a surgical treatment to treat various spine pathologies, such as those described herein.

Instrument 32 includes a first member, such as, for example, a sleeve 34 including an inner surface 36 defining a passageway 38. Sleeve 34 extends along a longitudinal axis a between a first end 40 and a second end 44. End 40 defines a first opening 42 and end 44 defines a second opening 46. Opening 46 includes an inner surface having a thread form configured to engage a thread form on a second member, such as, for example a shaft 60 to engage sleeve 34 with shaft 60, as will be described. Openings 42, 46 each have a circular cross section. Opening 42 has a diameter that is less than a diameter of opening 46. End 40 includes a threaded portion 45 extending from an outer surface of end 40 configured to engage an instrument, such as, for example, an extender. It is envisioned that the diameter of opening 42 may be greater than or equal to the diameter of opening 46. It is further envisioned that opening 42 and/or opening 46 may have alternate cross section configurations, such as, for example, oval, oblong, triangular, square, polygonal, irregular, uniform, non-uniform, offset, staggered, and/or tapered.

Sleeve 34 includes an intermediate portion 48 positioned between end 40 and end 44. End 40, end 44 and portion 48 each have a cylindrical cross sectional configuration. Portion 48 has a uniform diameter that is greater than the diameter of end 40 and less than the diameter of end 44. Sleeve 34 includes a first tapered portion 50 between end 40 and portion 48 and a second tapered portion 52 between portion 48 and end 44. In one embodiment, end 40 is tapered. It is envisioned that end 40, end 44 and/or portion 48 may be variously dimensioned and configured with respect to length, width, diameter and thickness. It is further envisioned that all or only a portion of end 40, end 44 and/or portion 48 may have alternate cross section configurations, such as, for example, oval, oblong, triangular, square, polygonal, irregular, uniform, non-uniform, offset, staggered, and/or tapered.

End 44 includes oblong fenestrations 54 extending through an exterior surface of sleeve 34 and surface 36 such that at least a portion of surface 36 and/or passageway 38 is/are visible through the exterior surface of sleeve 34. In one embodiment, sleeve 34 includes a plurality of fenestrations 54 circumferentially disposed about end 44 and equidistantly spaced apart. Fenestrations 54 each extend parallel to axis a. It is envisioned that fenestrations 54 may be variously configured and oriented about end 44, such as, staggered, consistent or variable, depending on the requirements of a particular application. It is further envisioned that fenestrations 54 may be disposed through angular ranges in various orientations relative to axis a, such as, for example, transverse or perpendicular and/or other angular orientations such as acute or obtuse, and/or may be offset or staggered. It is contemplated that fenestrations 54 may be variously configured and dimensioned, such as, for example, circular, oval, triangular, square, rectangular, polygonal, or irregular, depending on the requirements of a particular application. It is further contemplated that end 44 may include one, a plurality or no fenestrations 54.

Portion 48 includes oblong fenestrations 56 such that at least a portion of surface 36 and/or passageway 38 is/are visible through the exterior surface of sleeve 34. Portion 48 also includes oblong second fenestrations 58. In one embodiment, sleeve 34 includes a plurality of coaxial fenestrations 56 that are equidistantly spaced apart from one another and a plurality of coaxial fenestrations 58 that are equidistantly spaced part from one another. Fenestrations 56, 58 each extend parallel to axis a, with fenestrations 56 being offset from fenestrations 58. Fenestrations 56, 58 are parallel to fenestrations 54. In one embodiment, at least one of fenestrations 56 is coaxial with one of fenestrations 54 and at least one of fenestrations 58 is coaxial with another of fenestrations 54. It is envisioned that sleeve 34 may include one or a plurality of sets of fenestrations 56 and one or a plurality of sets of fenestrations 58, each of the sets of fenestrations 56, 58 being offset from one another. It is further envisioned that fenestrations 56 and/or fenestrations 58 may be disposed through angular ranges in various orientations relative to axis a, such as, for example, transverse or perpendicular and/or other angular orientations such as acute or obtuse, and/or may be offset or staggered. It is contemplated that fenestrations 56 and/or fenestrations 58 may be variously configured and dimensioned, such as, for example, circular, oval, triangular, square, rectangular, polygonal, or irregular, depending on the requirements of a particular application. It is further contemplated that portion 48 may include one, a plurality or no fenestrations 56 and/or fenestrations 58.

A second member, such as, for example, a shaft 60 extends between a first end 62 including a collar 64 and a second end 66 including a cap 68. Collar 64 has a diameter that is less than the diameter of opening 46 such that collar 64 can be inserted through opening 46 for positioning within passageway 38. Shaft 60 has a uniform diameter d at ends 62, 66 and includes an intermediate portion 70 positioned between ends 62, 66. Portion 70 has a diameter d1 that is less than diameter d.

Shaft 60 includes an outer sheath 72 having an inner surface defining a passageway configured for disposal of portion 70 such that an outer surface of portion 70 engages the inner surface of sheath 72 and collar 64 is rotatable relative to cap 68 such that rotating end 66 in the direction shown by arrow A or the direction shown by arrow AA, rotates end 62 and collar 64 in the same direction, without rotating cap 68. In one embodiment, cap 68 and sheath 72 are monolithically formed. In one embodiment, cap 68 is positioned on sheath 72 such that an inner surface of cap 68 engages an outer surface of sheath 72.

Cap 68 extends between a distal engagement portion 84 and a proximal crown portion 86. Portion 84 is configured for disposal in opening 46 to engage shaft 60 with sleeve 34. Portion 84 has a cylindrical cross section and a diameter that is slightly less than the diameter of opening 46. Portion 84 includes an outer surface 88 including a thread form configured to engage the thread form in opening 46 to engage shaft 60 with sleeve 34. Portion 86 has a diameter that is greater than that of opening 46 to prevent cap 68 from passing opening 46 and into passageway 38. It is envisioned that cap 68 may be disposed with sleeve 34 in alternate fixation configurations, such as, for example, friction fit, pressure fit, locking protrusion/recess, locking keyway and/or adhesive. It is contemplated that all or only a portion of cap 68 and/or sleeve 34 may have alternate surface configurations to enhance engagement with one another such as, for example, rough, arcuate, undulating, mesh, porous, semi-porous, dimpled and/or textured, according to the requirements of a particular application.

Portion 84 engages opening 46 and shaft 60 is engaged with sleeve 34 such that cap 68 may be rotated in the direction shown by arrow A such that shaft 60 moves in the direction shown arrow B and a distal face 90 of portion 84 engages a proximal face 92 of sleeve 34 for assembly of the component parts. Rotation of cap 68 in the direction shown by arrow AA causes cap 68 to move in the direction shown by arrow BB relative to sleeve 34 such that faces 90, 92 move away from one another for disassembly of the component parts. An outer surface of portion 86 has a diameter that is approximately equivalent to a diameter of an outer surface of end 44 such that the outer surfaces of portion 86 and end 44 form a continuous surface when face 90 engages face 92. It is envisioned that portion 86 may include one or more gaps or projections to facilitate gripping and rotation of portion 86 by a medical practitioner. It is further envisioned that such gaps or projections by extend parallel to axis a or may be disposed through angular ranges in various orientations relative to axis a, such as, for example, transverse or perpendicular and/or other angular orientations such as acute or obtuse, and/or may be offset or staggered.

Collar 64 includes a plurality of fingers 74 defining a socket 76 configured for disposal of a third member, such as, for example, a driver 78 to engage shaft 60 with driver 78. Fingers 74 are circumferentially disposed in a collet configuration about collar 64 and are equidistantly spaced apart. Adjacent fingers 74 are spaced apart by a gap 80 defined by opposite planar sidewalls. Adjacent sidewalls converge at an arcuate portion 82 configured to allow fingers 74 to move or deflect. Fingers 74 move such that a width of each gap 80 defined by a distance between the sidewalls may increase and decrease. It is envisioned that fingers 74 may be made from a resilient material to facilitate deflection of fingers 74 relative to one another.

In one embodiment, shaft 60 includes a drive portion 74 configured to engage an actuator to rotate shaft 60 in the direction shown by arrow A and/or the direction shown by arrow AA. It is envisioned that portion 74 may be configured to engage an actuator, such as, for example, a surgical instrument, powered drill, hand drill, driver or other tool to rotate shaft 60 in the direction shown by arrow A and/or the direction shown by arrow AA. In one embodiment, portion 74 has a tri-flat shape including a cross section having three planar surfaces arranged about an axis of portion 74. It is envisioned that portion 74 may include a square, hexagonal, polygonal, star or hexalobe cross sectional configuration configured engage a correspondingly shaped portion of the actuator.

Driver 78 extends between a first end, such as, for example, an implant driver 94 and a second end, such as, for example, a drive element 96. Drive element 96 is configured for disposal in socket 76 and has a diameter that is less than the diameter of opening 42 such that drive element 96 can be inserted through opening 42 and positioned within passageway 38 to engage collar 64 within passageway 38. Driver 94 includes a counter-torque bar, such as, for example, a T-bar portion 95 configured to releasably engage an implant, such as, for example, a bone fastener 98. Portion 95 has a diameter that is greater than the diameter of opening 42 such that portion 95 is prevented from passing through opening 42. Portion 95 is operable to engage fastener 98 while driver 78 is rotated about axis a in the direction shown by arrow A and/or the direction shown by arrow AA. As driver 78 is rotated about axis a, fastener 98 rotates about axis a in the same direction. Portion 95 is configured to disengage fastener 98 following fixation of fastener 98 with tissue, such as, for example, vertebrae. After portion 95 disengages fastener 98, instrument 32 may be withdrawn from the patient. It is contemplated that the implant may include a multi-axial bone screw, mono-axial bone screw, spinal rod, nail, staple, hook, rod, plate or intervertebral spacer.

Fastener 98 includes a proximal member 100 and a distal member 102 having a threaded outer surface configured to penetrate tissue, such as, for example, bone. Member 100 includes a pair of spaced apart arms 104. Arms 104 define a U-shaped cavity 106 therebetween configured for disposal of a spinal construct, such as, for example, a spinal rod. Portion 95 is configured for disposal in cavity 106. When portion 95 is disposed in cavity 106, an outer surface of portion 95 engages an inner surface of arms 104 defining cavity 106. In one embodiment, the outer surface of portion 95 is arcuate to mimic the arcuate shape of cavity 106. It is envisioned that portion 95 can be variously configured and dimensioned relative to cavity 106 with regard to length, width, diameter and thickness. In one embodiment, portion 95 has a length that is less than a length of cavity 106. In one embodiment, portion 95 has a length that is substantially the same as a length of cavity 106. In one embodiment, portion 95 has a length that is greater than a length of cavity 106. It is further envisioned that fastener 98 may include a mono-axial screw or multi-axial screw, depending upon the requirements of a particular application.

In one embodiment, cavity 106 includes an inner cavity (not shown) that is coaxial with member 102 and configured for disposal of a distal projection 108 of driver 94. The inner cavity of cavity 106 extends transverse to cavity 106. Driver 78 engages fastener 98 by first positioning projection 108 within the inner cavity of cavity 106 to engage driver 78 with fastener 98 and then positioning driver 95 within cavity 106 to prevent rotation of fastener 98 relative to driver 78. In one embodiment, projection 108 and the inner cavity each have complimentary hexagonal cross sections such that hexagonal projection 108 is disposed within the inner cavity and outer surfaces of projection 108 engage inner surfaces of the inner cavity. It is contemplated that projection 108 and the inner cavity may be variously configured and dimensioned, for example, projection 108 and the inner cavity may each include complimentary cruciform, square, hexagonal, polygonal, star or hexalobe cross sectional configurations.

Drive element 96 includes a hexalobular configuration defined by a plurality of splines 110 engageable with fingers 74 to prevent rotation of driver 78 relative to shaft 60. Adjacent splines 110 are separated by a recess 112. Driver 78 engages shaft 60 by positioning drive element 96 within socket 76 such that each spline 110 is positioned within a gap 80 and inner surfaces of fingers 74 engage outer surfaces of recesses 112. As splines 110 are inserted into gaps 80, the width of each gap 80 increases. Splines 110 are retained within gaps 80 as fingers 74 deflect and the width of gaps 80 decreases, capturing splines 110 within gaps 80. It is envisioned that drive element 96 may include at least two splines 110 and/or recesses 112. It is contemplated that the configuration of drive element 96 may be variously configured and dimensioned, for example, drive element 96 may include a cruciform, square, hexagonal, polygonal, star or hexalobe cross sectional configuration.

In assembly, operation and use, a surgical implant system, similar to system 30 described herein, is employed with a surgical procedure for treatment of a spinal disorder affecting a section of a spine of a patient, as discussed herein. For example, system 30 can be used with a surgical procedure for treatment of a condition or injury of an affected section of the spine including vertebrae (not shown). It is contemplated that one or all of the components of system 30 can be delivered or implanted as a pre-assembled device or can be assembled in situ. System 30 may be completely or partially revised, removed or replaced.

For example, system 30 can be employed with a surgical treatment of an applicable condition or injury of an affected section of a spinal column and adjacent areas within a body, such as, for example, vertebrae. It is envisioned that system 30 may be employed with one or a plurality of vertebra. To treat a selected section of the vertebrae, a medical practitioner obtains access to a surgical site including the vertebrae in any appropriate manner, such as through incision and retraction of tissues. It is envisioned that system 30 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of implantable components of system 30. A preparation instrument (not shown) can be employed to prepare tissue surfaces of vertebrae, as well as for aspiration and irrigation of a surgical region according to the requirements of a particular surgical application.

A pilot hole or the like is made in selected vertebrae for receiving an implant, such as, for example, a bone fastener 98. System 30 is disposed adjacent the vertebrae at a surgical site. The components of system 30 including instrument 32, are manipulable to drive, torque, insert or otherwise connect fastener 98 with the vertebrae, according to the particular requirements of the surgical treatment.

For example, the components of instrument 32 are assembled in that drive element 96 is advanced proximally through opening 42 and into passageway 38 and collar 64 is advanced distally through opening 46 and into passageway 38 such that collar 64 is adjacent drive element 96. Shaft 60 and/or driver 78 are manipulated such that collar 64 engages drive element 96 within passageway 38. As collar 64 engages drive element 96, splines 110 are positioned within gaps 80, as discussed above, so as to engage shaft 60 and driver 78 while preventing rotation of driver 78 relative to shaft. In one embodiment, the engagement between collar 64 and drive element 96 is visible through at least one of fenestrations 54 to allow a medical practitioner to visually confirm that driver 78 is properly engaged with shaft 60.

Driver 78 engages shaft 60 and cap 68 is positioned relative to sleeve 34 such that the thread form on surface 88 is aligned with the thread form in opening 46. Cap 68 is rotated in the direction shown by arrow A such that the thread form on surface 88 engages the thread from in opening 46 and cap 68 translates in the direction shown by arrow B. Cap 68 may be rotated in the shown by arrow A until face 90 engages face 92. In this configuration of instrument 32, drive element 96 is releasably engageable with collar 64 within passageway 38 such that end 40 of sleeve 34 prevents passage of T-bar 95 of driver 78 through opening 42 and end 44 of sleeve 34 prevents passage of cap 68 through opening 46. As such, shaft 60 and driver 78 are configured for rotation relative to sleeve 34 and cap 68 is configured to engage opening 46 to prevent axial translation of shaft 60 relative to driver 78.

Once access to the surgical site is obtained, the particular surgical procedure is performed. The components of system 30, including instrument 32 and fastener 98 are employed to augment the surgical treatment. For example, fastener 98 may be inserted into bone or other tissue with instrument 32. Fastener 98 may be delivered, introduced, inserted and/or removed from the bone or other tissue with instrument 32. For example, projection 108 is positioned within the inner cavity of cavity 106 to engage driver 78 and fastener 98 and driver 78 is positioned such that driver 95 engages cavity 106 to prevent rotation of fastener 98 relative to driver 78. Once driver 78 engages fastener 98, rotation of end 66, with or without an actuator or other tool, in the direction shown by arrow A or arrow AA causes driver 78 to rotate in the same direction such that fastener translates within bone or other tissue in the direction shown by arrow B or arrow BB, respectively. Upon completion of a surgical procedure, instrument 32 may be disengaged from fastener 98 by removing driver 95 from cavity 106 and projection 108 from the inner cavity of cavity 106, and the non-implanted components, including instrument 32 may be removed from the surgical site and the incision closed.

In one embodiment, the configuration of instrument 32 facilitates disassembly of its component parts to facilitate cleaning of one or all of the components of instrument 32. The collet configuration of shaft 60 and driver 78 facilitates disassembly such that collar 64 disengages from drive element 96, as described above. Shaft 60 is removed through opening 46 and driver 78 is removed through opening 42. The configuration of sleeve 34, shaft 60 and driver 78 allows shaft 60 to disengage driver 78 such that both shaft 60 and driver 78 can disengage sleeve 34. The individual components of instrument 32 can be cleaned, sterilized and/or otherwise treated according to the requirements of a particular surgical application. Instrument 32 may be re-assembled for use in a surgical procedure. It is envisioned that system 30 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

In one embodiment, system 30 includes an agent, which may be disposed, packed or layered within, on or about the components and/or surfaces of system 30. It is envisioned that the agent may include bone growth promoting material, such as, for example, bone graft to enhance fixation of the bone fasteners with the vertebrae. It is contemplated that the agent may include one or a plurality of therapeutic agents and/or pharmacological agents for release, including sustained release, to treat, for example, pain, inflammation and degeneration. The components of system 30 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 30.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including an inner surface defining a passageway and extending between a first end that defines a first opening and a second end that defines a threaded second opening;
   a second member comprising a shaft extending between a first end and a second end and a cap positioned between the first and second ends of the shaft, the cap being rotatable relative to the shaft and comprising a threaded outer surface that engages the threaded second opening to couple the second member with the first member; and
   a third member extending between a first end and a second end,
   wherein the second end of the third member is releasably engageable with the first end of the shaft within the passageway such that the first end of the first member prevents passage of the first end of the third member through the first opening and the second end of the first member prevents passage of the second end of the shaft through the second opening.

2. A surgical instrument as recited in claim 1, wherein the first end of the first member includes an enlarged outer surface and a distal face configured for engagement with the first end of the third member.

3. A surgical instrument as recited in claim 1, wherein the second end of the first member includes an enlarged outer surface and a proximal face configured for engagement with the second end of the third member.

4. A surgical instrument as recited in claim 1, wherein the second end of the third member is releasably engageable with the first end of the shaft such that the members are disposed in coaxial alignment.

5. A surgical instrument as recited in claim 1, wherein the third member is monolithic and the first end of the third member comprises a distalmost projection configured to engage an implant, the distalmost projection having a cross sectional configuration selected from a group consisting of hexagonal, cruciform, square, hexagonal, polygonal, star and hexalobe.

6. A surgical instrument as recited in claim 1, wherein the second end of the shaft is configured to engage an actuator.

7. A surgical instrument as recited in claim 1, wherein the first end of the third member includes a T-bar configuration defined by a pair of wings that extend outwardly from a cylindrical shaft of the third member and a tip of the shaft, the wings being positioned between the tip and the second end of the third member.

8. A surgical instrument as recited in claim 1, wherein the first end of the shaft includes a collar and the second end of the third member includes a hexalobular driver configured to engage the collar.

9. A surgical instrument as recited in claim 1, wherein the first end of the shaft includes fingers that are spaced apart from one another by gaps that extend through opposite inner and outer surfaces of the shaft, inner surfaces of the fingers jointly defining a socket configured for disposal of the second end of the third member, the second end of the third member comprising a plurality of splines that are positioned within the gaps to prevent rotation of the shaft relative to the third member.

10. A surgical instrument as recited in claim 1, wherein the first end of the shaft includes fingers that are spaced apart from one another by gaps that extend through inner and outer surfaces of the shaft, inner surfaces of the fingers jointly defining a socket, the second end of the third member including splines engageable with the socket, the fingers being deflectable to decrease widths of the gaps when the splines engage the socket to prevent rotation of the third member relative to the second member.

11. A surgical instrument as recited in claim 1, wherein the shaft and the third member are configured for rotation relative to the first member.

12. A surgical instrument as recited in claim 1, wherein the collar defines a socket and the drive element includes splines engageable with the socket to prevent rotation of the driver relative to the shaft.

13. A surgical instrument as recited in claim 1, wherein the first member comprises a plurality of coaxial fenestrations that are equidistantly spaced apart from one another.

14. A surgical instrument comprising:
a sleeve including an inner surface defining a passageway and extending between a first end that defines a first opening and a second end that defines a threaded second opening;
a shaft comprising a collar and a cap that is rotatable relative to the shaft, the cap comprising a threaded outer surface that engages the threaded second opening to couple the shaft with the first sleeve; and
a driver extending between an implant driver and a drive element,
wherein the drive element is releasably engageable with the collar within the passageway such that the first end of the sleeve prevents passage of the implant driver through the first opening and the second end of the sleeve prevents passage of the cap through the second opening.

15. A surgical instrument as recited in claim 14, wherein the first end of the sleeve includes an enlarged outer surface and a distal face configured for engagement with the implant driver.

16. A surgical instrument as recited in claim 14, wherein the second end of the sleeve includes an enlarged outer surface and a proximal face configured for engagement with the drive element.

17. A surgical instrument as recited in claim 14, wherein the drive element is releasably engageable with the collar such that the members are disposed in coaxial alignment.

18. A system comprising:
a bone fastener comprising a threaded shaft and a receiver coupled to the shaft, the receiver comprising a pair of spaced apart arms that define a U-shaped cavity therebetween; and
a surgical instrument comprising:
a sleeve including an inner surface defining a passageway and extending between a first end that defines a first opening and a second end that defines a second opening, the first end of the sleeve including an enlarged outer surface and a distal face, the second end of the sleeve including an enlarged outer surface and a proximal face;
a shaft comprising a collar and a cap that is rotatable relative to the shaft, the collar defining a socket; and
a driver extending between an implant driver and a drive element,
wherein the implant driver has a T-bar configuration defined by a pair of wings, the implant driver being configured for disposal in the cavity such that the wings are each positioned between the arms to prevent rotation of the bone fastener relative to the implant driver, the implant driver being configured for engagement with the distal face, the drive element including a hexalobular driver configured for engagement with the proximal face, the drive element including splines engageable with the socket to prevent rotation of the driver relative to the shaft, wherein the drive element is releasably engageable with the collar within the passageway such that the first end of the sleeve prevents passage of the implant driver through the first opening and the second end of the sleeve prevents passage of the cap through the second opening, wherein the shaft and the driver are configured for rotation relative to the sleeve, and wherein the cap is configured to engage the second opening to prevent axial translation of the shaft relative to the driver.

19. A system comprising:
the surgical instrument recited in claim 1; and
a bone fastener comprising a threaded shaft and a receiver coupled to the threaded shaft, the receiver comprising a pair of spaced apart arms defining a U-shaped cavity therebetween,
wherein the first end of the third member is disposed in the U-shaped cavity to prevent rotation of the bone fastener relative to the third member.

20. A system comprising:
the surgical instrument as recited in claim 1; and a bone fastener comprising a threaded shaft and a receiver coupled to the threaded shaft, the receiver comprising a pair of spaced apart arms having a hexagonal cavity therebetween, wherein the second end of the third member has a hexagonal projection configured for disposal in the hexagonal cavity to prevent rotation of the bone fastener relative to the third member.

* * * * *